United States Patent
Campin et al.

(10) Patent No.: US 7,226,443 B1
(45) Date of Patent: Jun. 5, 2007

(54) OPTIMIZATION OF ABLATION CORRECTION OF AN OPTICAL SYSTEM AND ASSOCIATED METHODS

(75) Inventors: John Alfred Campin, Orlando, FL (US); George H. Pettit, Maitland, FL (US); William T. Lefebvre, Oviedo, FL (US); Kevin K. Liedel, Orlando, FL (US)

(73) Assignee: Alcon RefractiveHorizons, Inc., Orlando, FL (US)

(*) Notice: Subject to any disclaimer, the term of this patent is extended or adjusted under 35 U.S.C. 154(b) by 133 days.

(21) Appl. No.: 10/740,374

(22) Filed: Dec. 18, 2003

Related U.S. Application Data (60) Provisional application No. 60/518,182, filed on Nov. 7, 2003.

(51) Int. Cl.
*A61F 9/008* (2006.01)

(52) U.S. Cl. .............................. 606/5; 128/898; 606/4

(58) Field of Classification Search ................ 128/898; 606/4–5
See application file for complete search history.

(56) References Cited

U.S. PATENT DOCUMENTS

| | | | |
|---|---|---|---|
| 4,420,228 A | 12/1983 | Humphrey | |
| 4,669,466 A | 6/1987 | L'Esperance | |
| 4,688,941 A | 8/1987 | Philbert | |
| 4,721,379 A | 1/1988 | L'Esperance | |
| 4,750,818 A | 6/1988 | Cochran | |
| 5,106,183 A | 4/1992 | Yoder, Jr. | |
| 5,221,834 A | 6/1993 | Lisson et al. | |
| 5,233,174 A | 8/1993 | Zmek | |
| 5,339,121 A | 8/1994 | Shimmick et al. | |
| 5,452,031 A | 9/1995 | Ducharme | |
| 5,493,391 A | 2/1996 | Neal et al. | |
| 5,581,347 A | 12/1996 | Le Saux et al. | |

(Continued)

FOREIGN PATENT DOCUMENTS

| | | |
|---|---|---|
| WO | WO 98/53881 | 12/1998 |
| WO | WO 99/27334 | 6/1999 |

OTHER PUBLICATIONS

Liang, et al., "Objective Measurement of Wave Aberrations of the Human Eye with the Use of a Hartmann-Shack Wave-front Sensor," *J. Opt. Soc. Am. A*, vol. 11, No. 7, Jul. 1994, pp. 1949-1957.

(Continued)

*Primary Examiner*—Henry M Johnson, III
(74) *Attorney, Agent, or Firm*—Allen, Dyer, Doppelt, Milbrath & Gilchrist, P.A.

(57) ABSTRACT

A method for optimizing a prescription for laser-ablation corneal treatment achieves the modification of wavefront-based refractive correction data with the use of user/doctor-input nomograms. Data comprising a wavefront description of a patient eye are received and displayed to a user, who can then make modifications to these treatment data. A modification is calculated based upon the desired correction to yield corrected wavefront description data, which are displayed to the user. A system includes a processor and a device for transmitting a wavefront description of a patient eye to the processor. An input device is adapted to receive a desired correction to the wavefront description data. Software is resident on the processor having code segments for implementing the calculations as described.

19 Claims, 8 Drawing Sheets

U.S. PATENT DOCUMENTS

| | | | |
|---|---|---|---|
| 5,632,742 | A | 5/1997 | Frey et al. |
| 5,666,492 | A | 9/1997 | Rhodes et al. |
| 5,684,545 | A | 11/1997 | Dou et al. |
| 5,722,427 | A | 3/1998 | Wakil et al. |
| 5,735,283 | A | 4/1998 | Snook |
| 5,777,719 | A | 7/1998 | Williams et al. |
| 5,782,822 | A | 7/1998 | Telfair et al. |
| 5,822,035 | A | 10/1998 | Bille |
| 5,841,511 | A | 11/1998 | D'Souza et al. |
| 5,849,006 | A | 12/1998 | Frey et al. |
| 5,949,521 | A | 9/1999 | Williams et al. |
| 6,095,651 | A | 8/2000 | Williams et al. |
| 6,129,722 | A | 10/2000 | Ruiz |
| 6,155,684 | A | 12/2000 | Bille et al. |
| 6,177,940 | B1 | 1/2001 | Bond et al. |
| 6,245,059 | B1 | 6/2001 | Clapham |
| 6,270,221 | B1 | 8/2001 | Liang et al. |
| 6,271,915 | B1 | 8/2001 | Frey et al. |
| 6,280,435 | B1 * | 8/2001 | Odrich et al. ............... 606/5 |
| 6,322,216 | B1 | 11/2001 | Yee et al. |
| 6,394,999 | B1 * | 5/2002 | Williams et al. ............ 606/5 |
| 6,413,251 | B1 | 7/2002 | Williams |
| 6,460,997 | B1 | 10/2002 | Frey et al. |
| 6,500,171 | B1 * | 12/2002 | Williams et al. ............ 606/5 |
| 6,582,078 | B2 | 6/2003 | Halpern et al. |
| 6,618,721 | B1 | 9/2003 | Lee |
| 6,814,729 | B2 * | 11/2004 | Youssefi et al. ............. 606/10 |
| 6,926,710 | B2 * | 8/2005 | Cox et al. .................... 606/5 |
| 7,146,983 | B1 * | 12/2006 | Hohla et al. ................ 128/898 |
| 2001/0041884 | A1 * | 11/2001 | Frey et al. .................... 606/5 |
| 2001/0053906 | A1 * | 12/2001 | Odrich et al. ................ 606/5 |
| 2002/0007176 | A1 * | 1/2002 | Campin et al. ............... 606/5 |
| 2002/0082629 | A1 * | 6/2002 | Cox et al. .................. 606/166 |
| 2003/0144650 | A1 * | 7/2003 | Smith .......................... 606/5 |
| 2003/0149597 | A1 | 8/2003 | Zaleski |
| 2003/0176855 | A1 * | 9/2003 | Gross et al. .................. 606/5 |
| 2003/0208190 | A1 * | 11/2003 | Roberts et al. ............... 606/5 |
| 2004/0002695 | A1 * | 1/2004 | Youssefi et al. .............. 606/5 |
| 2004/0054358 | A1 * | 3/2004 | Cox et al. .................... 606/5 |
| 2004/0116910 | A1 * | 6/2004 | Markman .................... 606/5 |

OTHER PUBLICATIONS

Roberts, "Characterization of the Inherent Error in a Spherically-Biased Corneal Topography System in Mapping a Radially Aspheric Surface," *Journal of Refractive & Corneal Surgery*, vol. 10, Mar./Apr. 1994, pp. 103-111.

Charman, "Wavefront Aberration of the Eye: A Review," *Optometry and Vision Science*, vol. 68, No. 8, pp. 574-583.

Gauthier, et al., "Factors Affecting Epithelial Hyperplasia After Photorefractice Keratectomy," *J Cataract Refract Surgery*, vol. 23, Sep. 1991, pp. 1042-1050.

Förster, MD, et al., "Steep Central Islands After Myopic Photorefractive Keratectomy," *J Cataract Refract Surgery*, vol. 24, Jul. 1998, pp. 899-904.

Munnerlyn, Ph.D., et al., "Photorefractive Keratectomy: A Technique for Laser Refractive Surgery" *J Cataract Refract Surgery*, vol. 14, Jan. 1988, pp. 46-52.

Wilson, "Structure of the Corneal Stroma," *Vision Res.*, vol. 10, Oct. 1969, pp. 519-520.

Vinciguerra, et al., "Photorefractive Keratoplasty I," Investigative Ophthamology & Visual Science, vol. 36, No. 4, pp. 81.

Jim Schwiegerling and John E. Greivenkkamp, "Using Corneal Heights Maps and Polynomial Decomposition to Determine Corneal Aberrations", Optometry and Vision Science, vol. 74, No. 11, pp. 906-916, Nov. 1997.

Peter Mierdel, et al., "Effects of Photorefractive Keratectomy And Cataract Surgery On Ocular Optical Errors Of Higher Order," Graefe's Arch Clin., Exp Ophthalmol, 237:725-729, Mar. 1999.

* cited by examiner

Custom doodad Screen

Protocol: Commercial / Clinical Trial A

Pending Wavefronts
- LastName FirstName OD 12/34/02
- LastName2 FirstName2 OS 12/34/02

← 16

[Delete] [Export] [UPDATE]

Trend Information/Wavefront Adjustments to be Applied — 17
Myopic  Sphere = + 10% -0.2D   Cylinder = +5%

Currently Selected Wavefront
| Last Name | FirstName | OD | 12/34/02 |

18 — Subjective Refraction           -2 / -1 x 30
19 — Wavefront-based Refraction      -2 / -1 x 30
20 — Post-Trend subjective Refraction -2 / -1 x 30

Additional Offsets
21 — Monovision  ○ Yes  ○ No    Monovision offset = 0.0
Additional Sphere  [Edit] — 22
Additional Cylinder at axis 30  [Edit] — 23

Effective Final Subjective Refraction = s.ss / c.cc x a

Depth Calculation
Optical Zone Diameter [Edit] — 24  Corneal Thickness [Edit] — 25  LASIK Flap Thickness [Edit] — 26

Central Ablation Depth = a bc um   Peak Ablation Depth = e lg um at r=3mm. theta=23 deg   Residual Stromal Thickness = 278um

↙ 14

| ID | Description | Type of Correction | SE Adjustment | Cyl. Adjustment |
|----|-------------|-------------------|---------------|-----------------|
| 3 | Commercial | 1 - Custom Cornea | Adjusted = Desired x 1.20 + 0.00 ← 27 | Adjusted = Desired x 0.80 + 0.00 ← 28 |

Rx Summary | Advanced | Nomograms

Apply    Edit

FIG. 4

Before Adjustment: +0.97D / -1.00D x 167
Net Offset: +0.24
After Adjustment: +1.21D / -1.00D x 171

OPTIMIZATION OF ABLATION CORRECTION OF AN OPTICAL SYSTEM AND ASSOCIATED METHODS

CROSS-REFERENCE TO RELATED APPLICATION

This application claims priority from commonly owned provisional application Ser. No. 60/518,182, filed Nov. 7, 2003, entitled "Implementing Nomograms to Allow for Modification of Wavefront-guided Procedures So as to Optimize Refractive Outcomes."

BACKGROUND OF THE INVENTION

1. Field of the Invention

The present invention relates to systems and methods for performing refractive laser surgery on the eye, and, more particularly, to such systems and methods that modify calculated treatment parameters to achieve an optimal ablation correction.

2. Description of Related Art

In conventional refractive laser surgery, a clinician typically modifies a prescription entered into the treatment system. Such modifications are based upon prior experience with outcomes achieved with that particular treatment system, and also upon experience with particular patient populations derived from, for example, demographic data. For example, a surgeon might enter a 2-diopter myopic treatment prescription for a patient diagnosed with 3 diopters of myopia if analysis of previous outcomes indicates a 50% overcorrection using this system for patients of a particular category. Such an empirical alteration of entered treatment parameters based upon previous experience is referred to as a nomogram adjustment. Nomograms are considered essential by the ophthalmic community because different clinicians employ different surgical techniques, operate under different environmental conditions, have distinct patient demographics, etc.

Conventional surgery involves a limited number of well-defined treatment parameters, principally spherical error, astigmatic error, astigmatic axis, optical zone size, and blend zone size. Thus it is relatively straightforward for a surgeon to develop nomogram formulas based on conventional clinical examinations before and after surgical procedures. In contrast, wavefront-guided customized treatments, such as that disclosed in commonly owned U.S. Pat. No. 6,270,221 B1, the disclosure of which is incorporated herein by reference, involve a complex mathematical description of the pre-operative aberration profile, which is transferred electronically to the treatment system.

In some currently used wavefront-based treatments, the raw wavefront data are modulated to generate a treatment profile in order to account for an apparent radial dependence in the effectiveness of ablative treatment on the corneal tissue. This, however, is currently applied substantially identically in all treatments. At present there is no known convenient method for a surgeon to modify a wavefront-based prescription prior to a procedure such as laser surgery.

In commonly owned patent applications Publication Nos. 2003/0078753 and 2003/0133074, the disclosures of which are incorporated herein by reference, two analytical methods for achieving ablation correction are disclosed based upon previously collected outcomes data.

SUMMARY OF THE INVENTION

The present invention is directed to a system and method for optimizing a prescription for laser-ablation corneal treatment. The method achieves the modification of wavefront-based refractive correction data with the use of user/doctor-input nomograms. The method comprises the steps of receiving data comprising a wavefront description of a patient eye, the data having been obtained previously. The wavefront description data are displayed to a user, who can then make modifications to these treatment data. A modification to the wavefront description data is calculated based upon the desired correction to yield corrected wavefront description data, which are then displayed to the user.

A further aspect of the present invention includes a method for determining whether a patient is an appropriate candidate for laser-ablation treatment, based upon a comparison of the corrected wavefront description data with predetermined criteria.

Another aspect of the present invention includes a software package for performing the method steps outlined above.

An additional aspect of the present invention includes a system for optimizing a prescription for laser-ablation corneal treatment. The system comprises a processor and means for transmitting a wavefront description of a patient eye to the processor. A display device and an input device are in signal communication with the processor. The input device is adapted to receive from the user a desired correction to the waterfront description data.

Software is resident on the processor having code segments for calculating a modification to the wavefront description data based upon the desired correction to yield corrected wavefront description data and implementing a display on the display device of the wavefront description and of the corrected wavefront description data.

The features that characterize the invention, both as to organization and method of operation, together with further objects and advantages thereof, will be better understood from the following description used in conjunction with the accompanying drawings. It is to be expressly understood that the drawing is for the purpose of illustration and description and is not intended as a definition of the limits of the invention. These and other objects attained, and advantages offered, by the present invention will become more fully apparent as the description that now follows is read in conjunction with the accompanying drawing.

DETAILED DESCRIPTION OF THE PREFERRED EMBODIMENTS

A description of the preferred embodiments of the present invention will now be presented with reference to FIGS. 1–9.

Figure 1:
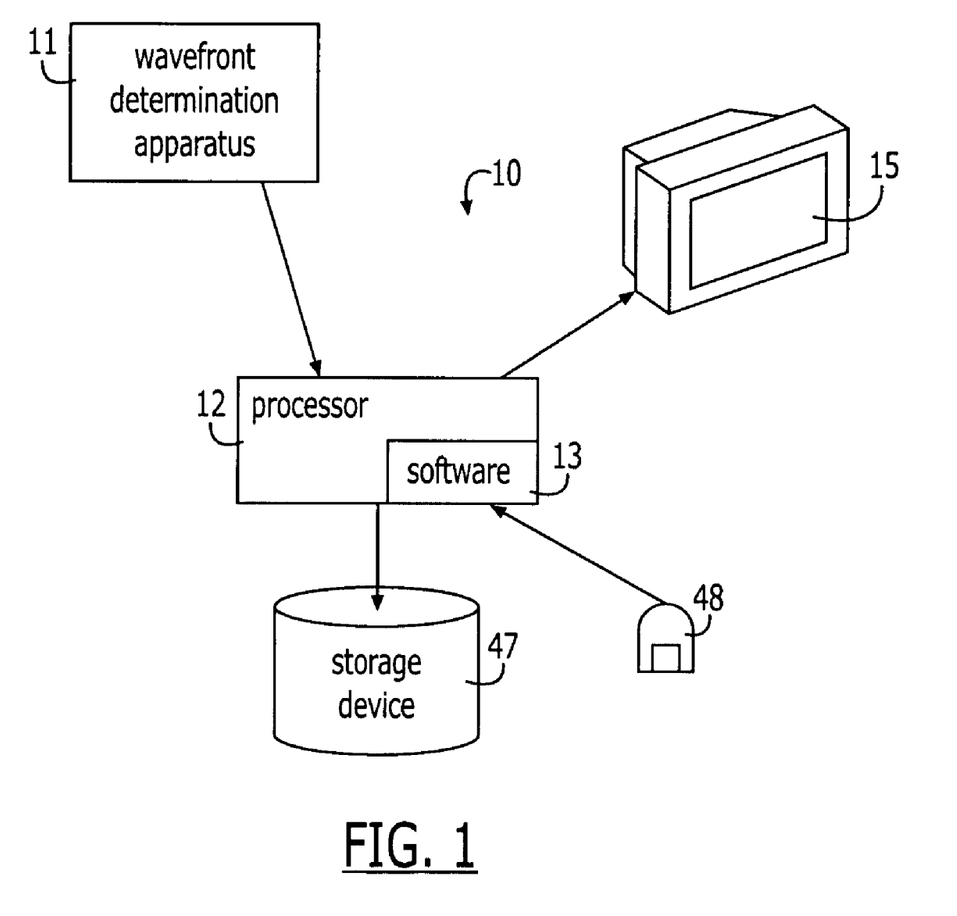
FIG. 1 is a schematic diagram of an exemplary embodiment of the system of the present invention.
Figure 2A:
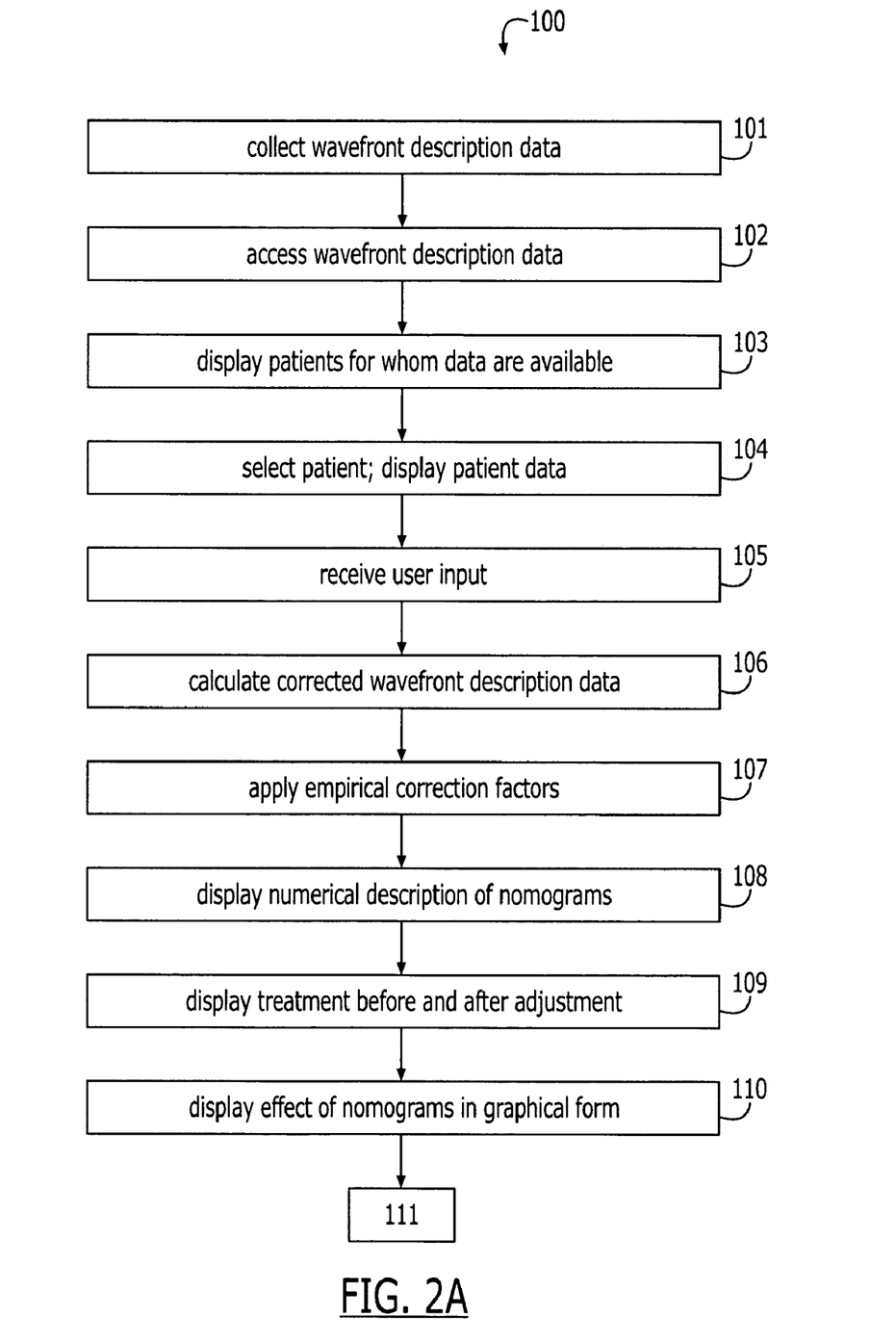
FIGS. 2A,2B is a flow chart of a method for optimizing a treatment prescription for a current patient in accordance with the present invention, to be referred to as hereafter as "FIG. 2."
Figure 2B:
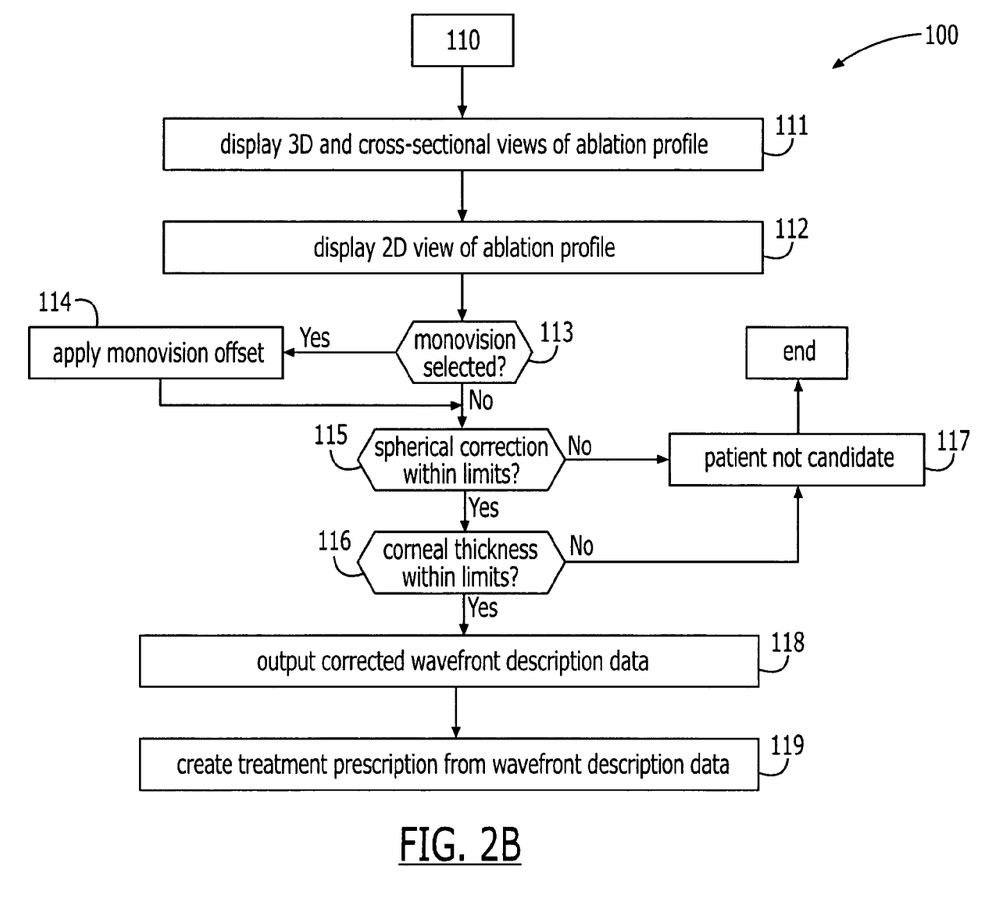
Figure 3:
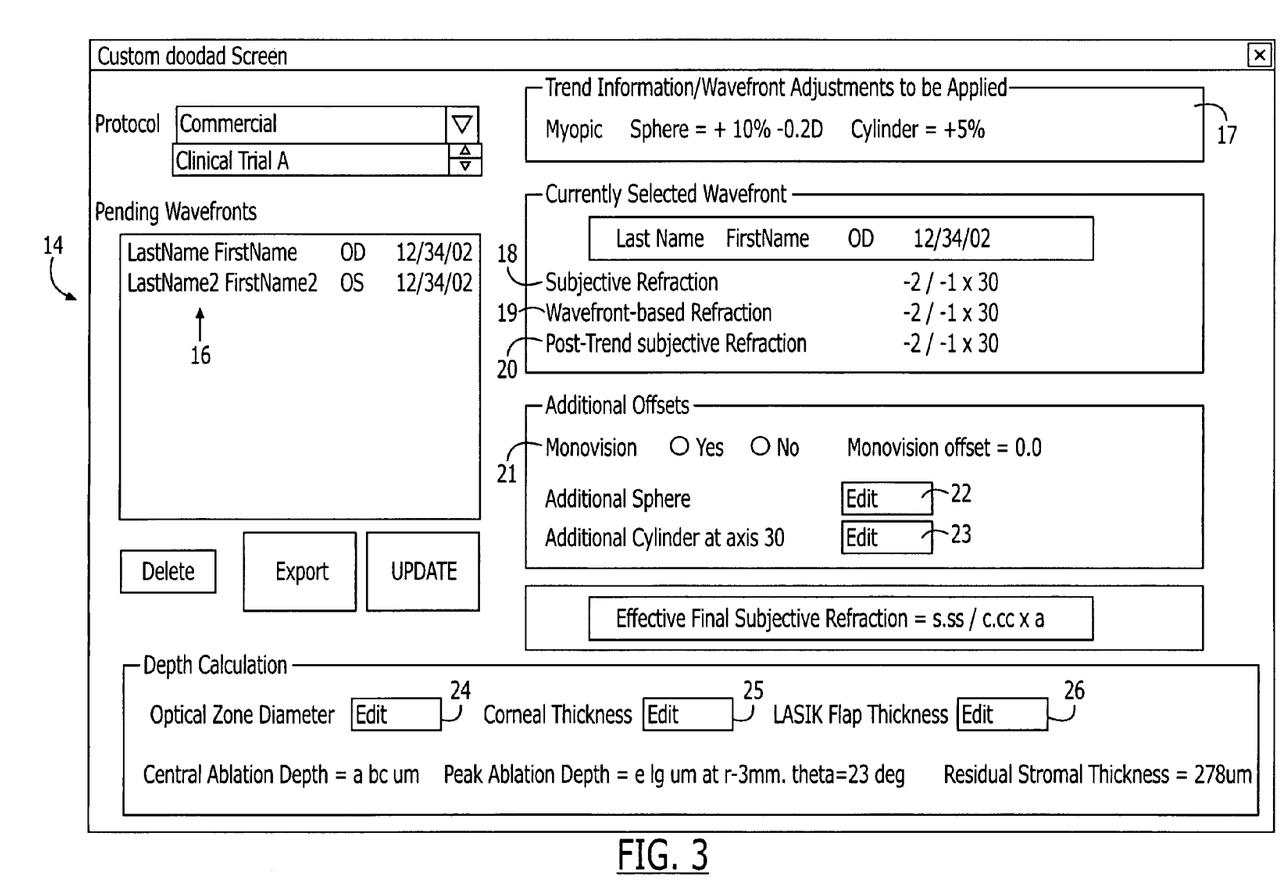
FIG. 3 is an exemplary graphical user interface for displaying data to and receiving input from a user.

The system 10 (FIG. 1) and method 100 (FIG. 2) of the present invention are directed, in a first aspect, to an optimization of a prescription for laser-ablation corneal treatment. In a preferred embodiment, wavefront description data from which a correction prescription can be calculated has been collected (block 101) using a wavefront determination apparatus 11 for a patient eye. Typically the wavefront description data comprise an algorithm having a plurality of terms, each of which has associated therewith a coefficient. For example, the wavefront may be described mathematically using a standardized form, such as Zernike polynomials, Taylor polynomilas, or Fourier series, although these are not intended as limitations. For any such form describing a mathematical shape, a specific wavefront can be described by the numerical values for the weighting of the various terms in the mathematical expression.

The wavefront determination data are accessed by a processor 12 housing a software package 13 for a current patient (block 102). These data may be obtained from, for example, a storage medium such as a volatile memory device (RAM or ROM, for example), or disk or a sector on a hard drive of the processor 12 or another processor in electronic communication therewith. In a preferred embodiment, a graphical user interface (GUI) 14 (FIG. 3) is presented on a display device 15. The GUI 14 preferably contains a list 16 of patients for whom wavefront determination data are available (block 103). Selection of an individual name, with the use of an input device 48 such as a mouse or other pointing device known in the art, causes a display of the selected patient's data (block 104) and other data, including information such as, but not intended to be limited to, trend information and adjustments to be applied 17, subjective refraction 18, wavefront-based refraction 19, and post-trend subjective refraction 20.

The GUI 14 can also contain areas for receiving user input (FIGS. 3 and 4; block 105), including, but not intended to be limited to, a selection to achieve monovision 21, spherical slope and offset 22, cylindrical slope 23, optical zone diameter 24, residual corneal thickness 25, and corneal flap thickness 26.

At block 106 of this embodiment of the method of the present invention, the software 13 then performs a calculation to modify the wavefront description data, such as by modifying accessed Zernike coefficients, based upon received user input. The software 13 may also apply a radial compensation functionality and a targeting matrix adjustment using a target-adjustment matrix resident on the processor 11. These adjustments comprise the application of empirically determined correction factors to the theoretically determined modifications (block 107).

Figure 4:
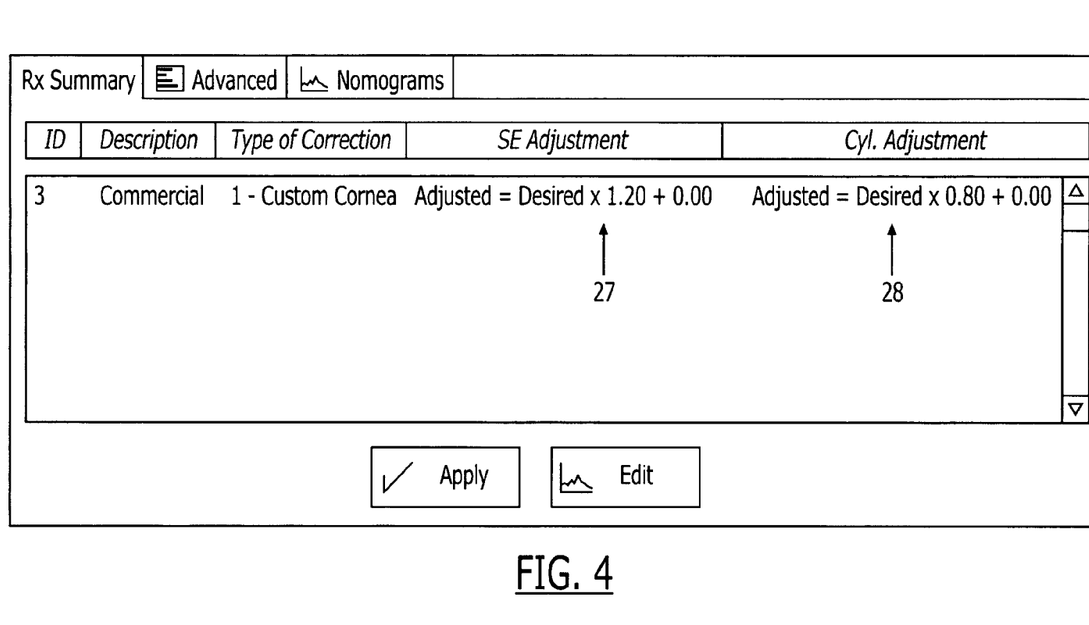
FIG. 4 displays a numerical description of specified spherical equivalent and cylindrical nomograms.
Figure 5:
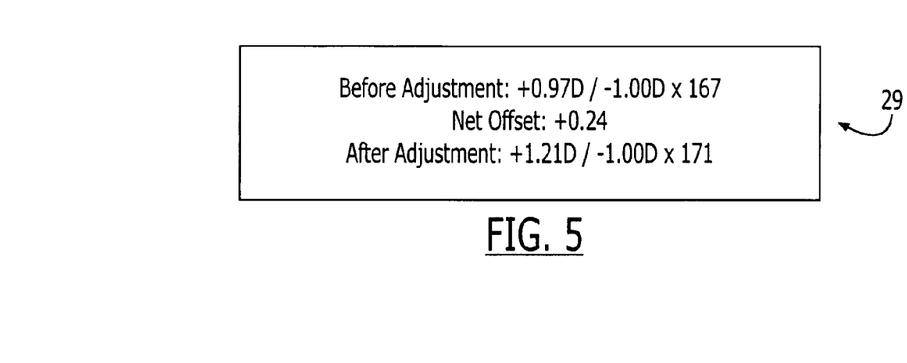
FIG. 5 displays an example of the spherical equivalent treatment before and after adjustment.
Figure 6A:
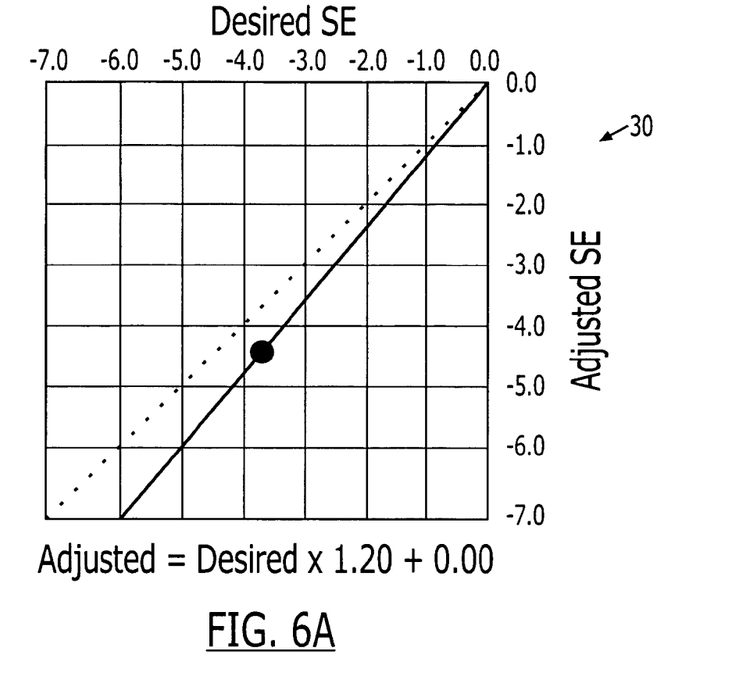
FIGS. 6A and 6B display, respectively, the effect of spherical equivalent and cylindrical nomograms.
Figure 6B:
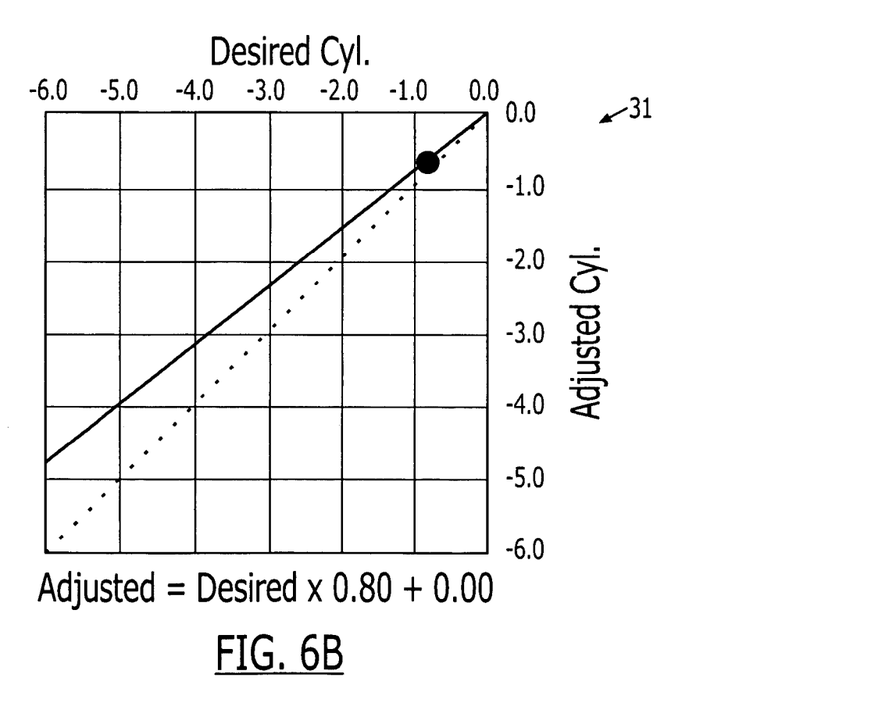
Figure 7:
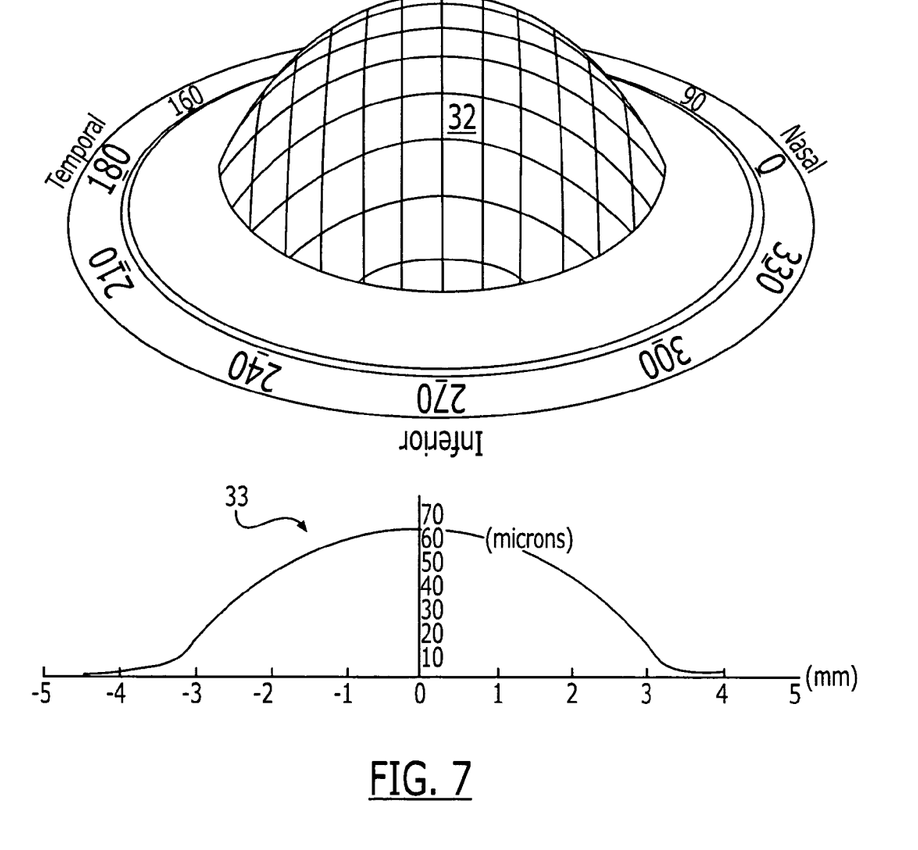
FIG. 7 displays on one screen a three-dimensional view of the calculated ablation profile and a cross-sectional view of the profile.
Figure 8:
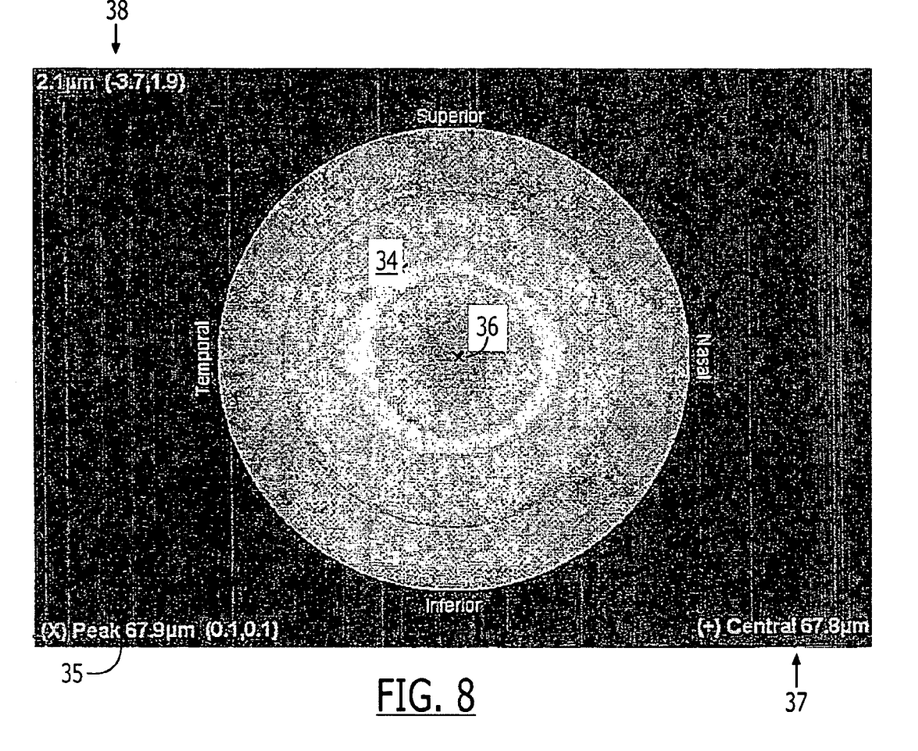
FIG. 8 displays a two-dimensional profile of the calculated ablations profile.
Figure 9:
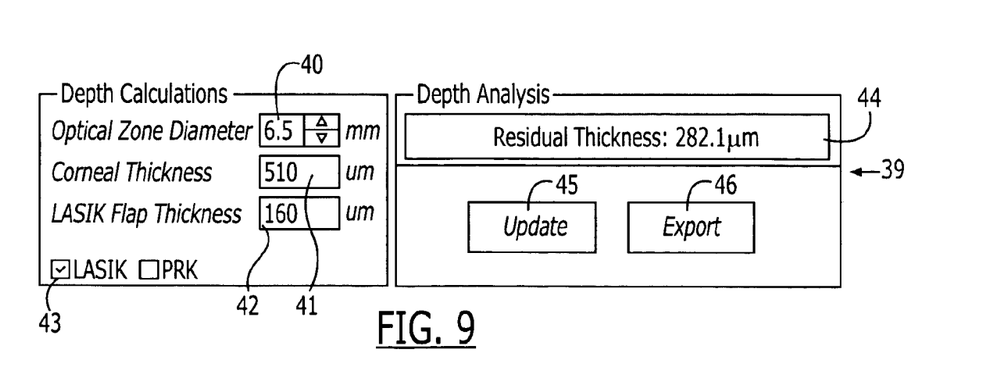
FIG. 9 displays depth/thickness data.

The results of these calculations are shown in FIGS. 4–9, which illustrate exemplary displays. FIG. 4, for example, illustrates a numerical description of specified spherical equivalent 27 and cylindrical 28 nomograms (block 108). FIG. 5 displays an example 29 of the spherical equivalent treatment before and after adjustment (block 109). FIGS. 6A and 6B display, respectively, the effect of spherical equivalent 30 and cylindrical 31 nomograms (block 110), wherein the dashed lines reflect no nomogram's being applied, the solid lines show the characteristics of the specified nomograms, and the circles show the effect of the nomograms on the currently selected eye. FIG. 7 displays on one screen a three-dimensional view of the calculated ablation profile 32 and a cross-sectional view 33 of the profile (block 111). FIG. 8 displays a two-dimensional view 34 (block 112), indicating peak depth 35, the location of the peak depth ("x") 36, the central depth 37, and the depth at the location of the cursor 38. FIG. 9 is a screen 39 displaying optical zone diameter 40, which can be adjusted by the user, corneal thickness 41, flap thickness 42, type of procedure 43, residual thickness 44, and buttons for updating 45 and exporting 46 data.

If a selection 21 (FIG. 3) has been made (block 113) for the treatment to achieve monovision, another calculation is performed by the software 13 to apply a predetermined offset (block 114).

When the calculations are complete, the software 13 compares the corrected wavefront description data with predetermined limiting values for permitting the treatment to proceed. For example, if the calculated spherical correction exceeds a predetermined maximum spherical correction (block 115), or if the calculated residual corneal thickness is less than a predetermined minimum residual corneal thickness (block 116), the patient eye is indicated as not being a candidate for treatment (block 117). Other data values can also have predetermined limits imposed thereon.

Once the calculations are complete and it has been determined that the patient eye is an acceptable candidate for the treatment, the corrected wavefront description data are output (block 118), for example, to a storage medium 47 such as a disk or another sector of the processor 12. These corrected data can then be used to create a treatment prescription for use in laser ablation surgery (block 119).

In the foregoing description, certain terms have been used for brevity, clarity, and understanding, but no unnecessary limitations are to be implied therefrom beyond the requirements of the prior art, because such words are used for description purposes herein and are intended to be broadly construed. Moreover, the embodiments of the system and method illustrated and described herein are by way of example, and the scope of the invention is not limited to the exact details disclosed herein.

Having now described the invention, the construction, the operation and use of preferred embodiment thereof, and the advantageous new and useful results obtained thereby, the new and useful constructions, and reasonable mechanical equivalents thereof obvious to those skilled in the art, are set forth in the appended claims.

What is claimed is:

1. A method for optimizing a prescription for laser-ablation corneal treatment comprising the steps of:

receiving data comprising a wavefront description of a patient eye;

displaying to a user the wavefront description data;

receiving from the user a desired correction to the wavefront description data, wherein the corrected wavefront description data comprise a spherical correction;

calculating a modification to the wavefront description data based upon the desired correction to yield corrected wavefront description data;

comparing the spherical correction with a predetermined upper limit on spherical correction, and, if the spherical correction exceeds the predetermined upper limit, indicating to the user that the spherical correction is not acceptable; and displaying to the user the corrected wavefront description data.

2. The method recited in claim 1, wherein the data-receiving step comprises receiving into a processor a Zernike polynomial description of a patient eye wavefront.

3. The method recited in claim 1, wherein the modification-calculating step comprises performing the calculating under control of software resident on a processor, and further comprising the step, following the modification-calculating step, of saving to a storage medium the corrected wavefront description data.

4. A method of optimizing a prescription for laser-ablation corneal treatment comprising the steps of:
receiving data comprising a wavefront description of a patient eye;
displaying to a user the wavefront description data;
receiving from the user a desired correction to the wavefront description data;
calculating a modification to the wavefront description data based upon the desired correction to yield corrected wavefront description data;
comparing the corrected wavefront description data with predetermined criteria for laser-ablation corneal treatment, and, if the predetermined criteria are not met, indicating to the user that the patient eye is not an acceptable candidate for the treatment; and
displaying to the user the corrected wavefront description data.

5. The method recited in claim 4, further comprising the step, following the calculating step, of computing at least one of an optical zone diameter, a peak ablation depth, a central ablation depth, and a location of the peak ablation depth on a pupil of the patient eye.

6. The method recited in claim 4, wherein the receiving step further comprises receiving from the user a selection to calculate the modification including an option to achieve monovision.

7. The method recited in claim 6, wherein, if the user has made the selection for monovision, displaying a preselected offset for achieving monovision.

8. The method recited in claim 4, wherein the receiving step further comprises receiving from the user a user-specified offset for achieving monovision.

9. The method recited in claim 4, wherein the corrected wavefront description data comprise an ablation profile, and wherein the corrected wavefront description data displaying step comprises displaying a graphical representation of the ablation profile.

10. The method recited in claim 9, wherein the ablation profile graphical representation comprises at least one of a three-dimensional representation, a two-dimensional representation, and a cross-sectional representation of the ablation profile.

11. A method for optimizing a prescription for laser-ablation corneal treatment comprising the steps of:
receiving data comprising a wavefront description of a patient eye;
displaying to a user the wavefront description data;
receiving from the user a desired correction to the wavefront description data;
calculating a modification to the wavefront description data based upon the desired correction to yield corrected wavefront description data;
computing a residual corneal thickness and a corneal flap thickness; and
displaying to the user the corrected wavefront description data.

12. The method recited in claim 11, further comprising the step, following the computing step, of comprising the residual corneal thickness with a predetermined minimum corneal thickness, and, if the residual corneal thickness is less than the predetermined minimum corneal thickness, indicating to the user that the patient eye is not an acceptable candidate for the treatment.

13. The method recited in claim 11, wherein the wavefront description data displaying step comprises displaying measured sphero-cylindrical data and a first corrective prescription calculated from the sphero-cylindrical data, and wherein the corrected wavefront description data comprise a second corrective prescription.

14. The method recited in claim 13, wherein the sphero-cylindrical data comprises at least one of subjective refraction, wavefront-based refraction, and post-trend subjective refraction.

15. The method recited in claim 13, wherein the correction-receiving step comprises receiving a desired correction to the sphero-cylindrical data.

16. A method for determining candidacy for a wavefront-based corneal ablation treatment on an eye comprising the steps of:
receiving data comprising a wavefront description of a patient eye;
displaying to a user the wavefront description data;
receiving from the user a desired correction to the wavefront description data;
calculating a modification to the wavefront description data based upon the desired correction to yield corrected wavefront description data;
comparing the corrected wavefront description data with predetermined criteria for corneal ablation treatment; and
if the predetermined criteria are not met by the corrected wavefront description data, indication to the user that the patient eye is not an acceptable candidate for the treatment.

17. A system for optimizing a prescription for laser-ablation corneal treatment comprising:
a processor;
means for transmitting a wavefront description of a patient eye to the processor;
a display device in signal communication with the processor;
an input device in signal communication with the processor adapted to receive from the user a desired correction to the wavefront description data; and
software resident on the processor having code segments for:
calculating a modification to the wavefront description data based upon the desired correction to yield corrected wavefront description data, the modification comprising at least one of a spherical equivalent and a cylindrical nomograms;
comparing the corrected wavefront description data with predetermined criteria for laser-ablation corneal treatment, and, if the predetermined criteria are not met, indicating to the user that the patient eye is not an acceptable candidate for the treatment; and
implementing a display on the display device of the wavefront description and of the corrected wavefront description data.

18. The system recited in claim 17, wherein the implementing code segment comprises code for displaying a graphical user interface containing the wavefront description data and containing an area for electronically entering the desired correction thereonto.

19. The system recited in claim 18, wherein the interface further contains an area for electronically entering a selection to calculate corrected wavefront description data for achieving monovision, and wherein the calculating code segment further comprises code for adjusting the corrected wavefront description data to achieve monovision.

* * * * *